United States Patent [19]

Herbst et al.

[11] Patent Number: 5,763,474

[45] Date of Patent: Jun. 9, 1998

[54] SUBSTITUTED N-ARYLMETHYLAMINO DERIVATIVES OF CYCLOBUTENE-3,4-DIONES

[75] Inventors: David R. Herbst, Wayne, Pa.; Madelene M. Antane, Lawrenceville, N.J.; Geraldine R. McFarlane, Monmouth Junction, N.J.; Eric G. Gundersen, Plainsboro, N.J.; Bradford H. Hirth, Littleton, Mass.; Dominick A. Quagliato, Bridgewater, N.J.; Russell F. Graceffa, Plainsboro, N.J.; John A. Butera, Clarksburg, N.J.

[73] Assignee: American Home Products Corporation, Madison, N.J.

[21] Appl. No.: 889,164

[22] Filed: Jul. 7, 1997

Related U.S. Application Data

[60] Provisional application No. 60/022,113 Jul. 17, 1996.

[51] Int. Cl.[6] .................... A61K 31/135; A61K 31/165; C07C 225/20; C07C 235/82

[52] U.S. Cl. .................. 514/399; 514/487; 514/522; 514/524; 514/562; 514/563; 514/564; 514/604; 514/605; 514/616; 514/617; 514/629; 514/655

[58] Field of Search ................ 564/82, 92, 99, 564/155, 182, 184, 207, 218, 306; 562/162, 164; 560/13, 27; 558/417, 418; 548/341.1; 514/399, 487, 522, 524, 562, 563, 564, 604, 605, 616, 617, 629, 655

[56] References Cited

U.S. PATENT DOCUMENTS

| | | | |
|---|---|---|---|
| 4,390,701 | 6/1983 | Algieri et al. | 546/335 |
| 4,673,747 | 6/1987 | Nobara et al. | 546/334 |
| 5,240,946 | 8/1993 | Kinney et al. | 514/364 |
| 5,354,746 | 10/1994 | Chandrakumar et al. | 514/211 |
| 5,354,763 | 10/1994 | Butera et al. | 514/352 |
| 5,397,790 | 3/1995 | Butera et al. | 514/310 |
| 5,401,753 | 3/1995 | Butera et al. | 514/311 |
| 5,403,853 | 4/1995 | Butera et al. | 514/399 |
| 5,403,854 | 4/1995 | Butera et al. | 514/415 |
| 5,464,867 | 11/1995 | Antane et al. | 514/524 |
| 5,466,712 | 11/1995 | Butera et al. | 514/524 |
| 5,506,252 | 4/1996 | Butera et al. | 514/399 |
| 5,512,585 | 4/1996 | Antane et al. | 514/352 |
| 5,530,025 | 6/1996 | Antane et al. | 514/522 |
| 5,532,245 | 7/1996 | Butera et al. | 514/272 |
| 5,536,731 | 7/1996 | Antane et al. | 514/307 |
| 5,536,741 | 7/1996 | Antane et al. | 514/394 |

FOREIGN PATENT DOCUMENTS

| | | |
|---|---|---|
| 426379 | 10/1990 | European Pat. Off. |
| 496561 | 1/1992 | European Pat. Off. |
| 645385 | 3/1995 | European Pat. Off. |

OTHER PUBLICATIONS

Tietze et al., Chem. Berg., 1991, 124, 1215–1221.
Tietze et al., Bioconjugate Chem., 1991, 2, 148–153.
Ehrhardt et al., Chem. Ber., 1977, 110, 2506–2523.
Neuse et al., Liebigs Ann. Chem., 1973, 619–632
Takeno et al. Public Patent Disclosure Bull. No 6-92915 (Japan) 1994.
Reid et al., Liebigs Ann. Chem. 1981, 402.
Kinney et al., J. Med. Chem., 1992, 35, 4720.

*Primary Examiner*—Richard L. Raymond
*Attorney, Agent, or Firm*—Rebecca R. Barrett

[57] ABSTRACT

The compounds of the formula:

wherein $R_1$ is straight chain alkyl, branched chain alkyl cycloalkyl, hydroxyalkyl, fluoroalkyl or polyfluoroalkyl; $R_2$ and $R_3$ are, independently, hydrogen or an acyl substituent selected from the group consisting of formyl, alkanoyl, alkenoyl, alkoxycarbonyl, alkylsulfonyl, aroyl, arylalkenoyl, arylsulfonyl, arylalkanoyl or arylalkylsulfonyl; A is a substituted phenyl group of the following formula:

wherein $R_4$ and $R_5$ are, independently, cyano, nitro, amino, alkyl, perfluoroalkyl, fluoroalkyl, alkoxy, perfluoroalkoxy, fluoroalkoxy, amino, alkylamino, dialkylamino, sulfamyl, alkylsulfonamido, arylsulfonamido, carbamoyl, alkylcarbamoyl, dialkylcarbamoyl, alkylcarboxamido, arylcarboxamido, alkylsulfonyl, perfluoroalkylsulfonyl, arylsulfonyl, chloro, bromo, fluoro, iodo, 1-imidazolyl, carboxyl or hydrogen, with the proviso that $R_4$ and $R_5$ cannot both be hydrogen; or a pharmaceutically acceptable salt thereof, relaxes smooth muscles.

27 Claims, No Drawings

SUBSTITUTED N-ARYLMETHYLAMINO DERIVATIVES OF CYCLOBUTENE-3,4-DIONES

This application claims the benefit of U.S. application Ser. No. 60/022,113, filed Jul. 17, 1996 and is a continuation-in-part of that prior application which is incorporated by reference herein in its entirety.

BACKGROUND OF THE INVENTION

The present invention relates to novel 1, 2-diamino derivatives of cyclobutene 3,4-diones having pharmacological activity, to a process for their preparation, to pharmaceutical compositions containing them and to their use, via potassium channel modulation, in the treatment of disorders associated with smooth muscle contraction. Such disorders include, but are not limited to, urinary incontinence, hypertension, asthma, premature labor, irritable bowel syndrome, congestive heart failure, angina and cerebral vascular disease.

Stemp et al. (EP-426379) disclose a class of amino substituted cyclobutenedione derivatives of chromas described as having blood pressure lowering activity and bronchodilatory activity. Takeno et al. (Public Patent Disclosure Bulletin No. 6-92915) report a series of diaminocyclobuten-3,4-diones. Our own efforts in this area have been disclosed in the following U.S. Pat. Nos.: 5,354,763, 5,397,790, 5,401,753, 5,403,853, 5,403,854, 5,506,252; 5,466,712, 5,532,245; 5,464,867, 5,512,585, 5,530,025, 5,536,731, 5,536,741. Several series of 1-amino-2-phenylalkylamino-cyclobutene-3,4-diones are reported as H-2 receptor antagonists by Algieri et al. in U.S. Pat. No. 4,390,701. Several related 1-amino-2-phenoxyalkylamino derivatives are disclosed by Nohara et al. in U.S. Pat. No. 4,673,747. Additionally, U.S. Pat. No. 5,240,946 and EP-496561 disclose diaminocyclobuten-3,4-diones useful as NMDA antagonists.

The syntheses of variously substituted 1,2-diaminocyclobutene-3,4-diones are described in the following publications: Tietze et al., Chem Ber. 1991, 124, 1215; Tietze et al., Bioconjugate Chem. 1991, 2, 148; Ehrhardt et al., Chem. Ber. 1977, 110, 2506, Neuse et al., Liebigs Ann. Chem. 1973, 619, Ried et al., Liebigs Ann. Chem. 1973, 619, Kinney et al., J. Med. Chem. 1992, 35, 4702.

DESCRIPTION OF THE INVENTION

Accordingly, the present invention discloses compounds represented by formula (I):

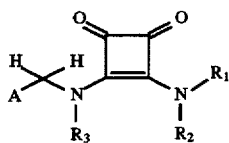

(I)

wherein:

$R_1$ is straight chain alkyl of 1 to 10 carbon atoms, branched chain alkyl of 3 to 10 carbon atoms, cycloalkyl of 3 to 10 carbon atoms, hydroxyalkyl of 2 to 10 carbon atoms, fluoroalkyl of 1 to 10 carbon atoms or polyfluoroalkyl of 1 to 10 carbon atoms;

$R_2$ and $R_3$ are, independently, hydrogen or an acyl substituent selected from the group consisting of formyl, alkanoyl of 2 to 7 carbon atoms, alkenoyl of 3 to 7 carbon atoms, straight chain alkoxycarbonyl of 2 to 11 carbon atoms, branched chain alkoxycarbonyl of 4 to 11 carbon atoms, cycloalkoxycarbonyl of 4 to 11 carbon atoms, alkenoxycarbonyl of 2 to 11 carbon atoms, aralkoxycarbonyl of 6 to 12 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms; with the proviso that when $R_3$ is straight chain alkoxycarbonyl of 2 to 11 carbon atoms, branched chain alkoxycarbonyl of 4 to 11 carbon atoms, cycloalkoxycarbonyl of 4 to 11 carbon atoms, alkenoxycarbonyl of 2 to 11 carbon atoms or aralkoxycarbonyl of 6 to 12 carbon atoms, $R_2$ must be hydrogen.

A is a substituted phenyl group of the following formula:

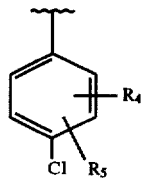

wherein:

$R_4$ and $R_5$ are, independently, cyano, nitro, amino, alkyl of 1 to 6 carbon atoms, perfluoroalkyl of 1 to 6 carbon atoms, fluoroalkyl of 1 to 6 carbon atoms, alkoxy of 1 to 6 carbon atoms, perfluoroalkoxy of 1 to 6 carbon atoms, fluoroalkoxy of 1 to 6 carbon atoms, alkylamino of 1 to 6 carbon atoms, dialkylamino of 2 to 12 carbon atoms, sulfamyl, alkylsulfonamido of 1 to 6 carbon atoms, arylsulfonamido of 6 to 12 carbon atoms, carbamoyl, alkylcarbamoyl of 2 to 7 carbon atoms, dialkylcarbamoyl of 4 to 14 carbon atoms, alkylcarboxamido containing 2 to 7 carbon atoms, arylcarboxamido containing 7 to 13 carbon atoms, alkylsulfonyl of 1 to 6 carbon atoms, perfluoroalkylsulfonyl of 1 to 6 carbon atoms, arylsulfonyl of 6 to 12 carbon atoms, chloro, bromo, fluoro, iodo, 1-imidazolyl, carboxyl or hydrogen, with the proviso that $R_4$ and $R_5$ cannot both be hydrogen;

or a pharmaceutically acceptable salt thereof.

A preferred aspect of this invention involves compounds of formula (I) wherein:

$R_1$ is straight chain alkyl of 1 to 10 carbon atoms, branched chain alkyl of 3 to 10 carbon atoms, fluoroalkyl of 1 to 10 carbon atoms or perfluoroalkyl of 1 to 10 carbon atoms;

$R_2$ and $R_3$ are, independently, hydrogen, alkanoyl of 2 to 7 carbon atoms, alkenoyl of 3 to 7 carbon atoms, aroyl of 7 to 12 carbon atoms, arylalkenoyl of 9 to 20 carbon atoms, straight chain alkoxycarbonyl of 2 to 7 carbon atoms, branched chain alkoxycarbonyl of 4 to 7 carbon atoms, alkenoxycarbonyl of 4 to 7 carbon atoms, or aralkoxycarbonyl of 6 to 12 carbon atoms; with the proviso that when $R_3$ is straight chain alkoxycarbonyl of 2 to 7 carbon atoms, branched chain alkoxycarbonyl of 4 to 7 carbon atoms, alkenoxycarbonyl of 4 to 7 carbon atoms, or aralkoxycarbonyl of 6 to 12 carbon atoms, $R_2$ must be hydrogen;

A is a substituted phenyl group of the following formula:

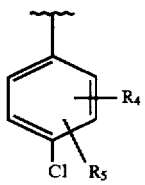

wherein:

R$_4$ and R$_5$ are, independently, cyano, alkyl of 1 to 6 carbon atoms, perfluoroalkyl of 1 to 6 carbon atoms, fluoroalkyl of 1 to 6 carbon atoms, alkoxy of 1 to 6 carbon atoms, perfluoroalkoxy of 1 to 6 carbon atoms, fluoroalkoxy of 1 to 6 carbon atoms, chloro, bromo, fluoro, iodo or hydrogen, with the proviso that R$_4$ and R$_5$ cannot both be hydrogen;

or a pharmaceutically acceptable salt thereof.

The most preferred aspect of this invention includes compounds of formula (I) wherein:

R$_1$ is branched chain alkyl of 3 to 10 carbon atoms or fluoroalkyl of 1 to 10 carbon atoms;

R$_2$ and R$_3$ are, independently, hydrogen, alkanoyl of 2 to 7 carbon atoms, alkenoyl of 3 to 7 carbon atoms, straight chain alkoxycarbonyl of 3 or 5 carbon atoms, branched chain alkoxycarbonyl of 5 carbon atoms, alkenoxycarbonyl of 4 carbon atoms, or aralkoxycarbonyl of 8 carbon atoms; with the proviso that when R$_3$ is straight chain alkoxycarbonyl of 3 or 5 carbon atoms, branched chain alkoxycarbonyl of 5 carbon atoms, alkenoxycarbonyl of 4 carbon atoms, or aralkoxycarbonyl of 8 carbon atoms, R$_2$ must be hydrogen;

A is a substituted phenyl group of the following formula:

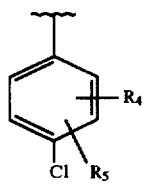

wherein:

R$_4$ and R$_5$ are, independently, cyano, methyl, ethyl, trifluoromethyl, fluoroalkyl of 1 to 2 carbon atoms, methoxy, ethoxy, trifluoromethoxy, fluoroalkoxy of 1 to 2 carbon atoms, chloro, bromo, fluoro or hydrogen, with the proviso that R$_4$ and R$_5$ cannot both be hydrogen;

or a pharmaceutically acceptable salt thereof.

It is understood that the definition of the compounds of formula (I), when R$_1$, R$_2$, R$_3$, R$_4$, or R$_5$ contain asymmetric carbon atoms, encompass all possible stereoisomers and mixtures thereof which possess the activity discussed below. In particular, it encompasses racemic modifications and any optical isomers which possess the indicated activity. Optical isomers may be obtained in pure form by standard separation techniques. The pharmaceutically acceptable salts are those derived from such organic and inorganic acids as: lactic, citric, acetic, tartaric, succinic, maleic, malonic, hydrochloric, hydrobromic, phosphoric, nitric, sulfuric, methanesulfonic and similarly known acceptable acids.

The present invention also provides a process for the preparation of a compound of formula (I). More particularly, the compounds of formula (I) may be prepared by reacting a compound of formula (II):

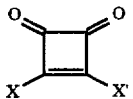 (II)

wherein X and X' is a suitably designed leaving group such as methoxy, ethoxy, butoxy, isopropoxy, halogeno or a similar leaving group, with a compound of formula (III):

 (III)

wherein A$_1$ is A, as defined hereinbefore or a group of atoms convertible thereto, followed by treatment with a compound of formula (IV):

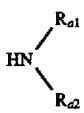 (IV)

wherein R$_{a1}$ and R$_{a2}$ are R$_1$ and R$_2$, respectively, as defined hereinbefore or a group of atoms convertible thereto in a solvent such as ethanol, acetonitrile, tetrahydrofuran or the appropriate amine (IV) at elevated temperatures or room temperature. Dichloromethane can be used as a cosolvent. The order of addition of compound of formula (III) and compound of formula (IV) to a compound of formula (II) may be reversed. Furthermore reaction of the sodium, potassium, or lithium salt of the compound of formula (II) where X is NHCH$_2$—A attached to the cyclobutene group through the nitrogen where A is defined above, and X' is NHR$_1$ attached to the cyclobutene group through the nitrogen where R$_1$ is as defined above, with the appropriate anhydride in tetrahydrofuran and/or N,N-dimethylformamide allows for the attachment of R$_3$. Reaction of sodium, potassium, or lithium salt of compound of formula (II), where X is a leaving group such as methoxy, ethoxy, butoxy, isopropoxy, or similar leaving group and X' is NHR$_1$ attached to the cyclobutene group through the nitrogen where R$_1$ is as defined above, with the appropriate anhydride in dichloromethane, tetrahydrofuran and/or N,N-dimethylformamide or any other suitable solvent, followed by treatment with a compound of formula (III) as defined above in a solvent such as acetonitrile at room temperature allows for the attachment of the acyl groups represented by R$_2$.

Alternatively, reaction of sodium, potassium or lithium salt of a compound of formula (II), where X is a leaving group such as methoxy, ethoxy, butoxy, isopropoxy, or similar leaving group; and X' is NHCH$_2$—A attached to the cyclobutene group through the nitrogen where A is as defined above, with the appropriate dialkyl dicarbonate in the presence of triethylamine, 4-dimethylaminopyridine and a suitable solvent such as dichloromethane, tetrahydrofuran and/or N,N-dimethylformamide, followed by treatment with a compound of formula (III) as defined above in a solvent such as acetonitrile or tetrahydrofuran at room temperature allows for the attachment of the alkoxycarbonyl groups represented by R$_3$.

As mentioned previously, the compounds of formula (I) have been found to relax smooth muscle. They are therefore useful in the treatment of disorders associated with smooth muscle contraction, disorders involving excessive smooth muscle contraction of the urinary tract (such as incontinence) or of the gastrointestinal tract (such as irritable bowel syndrome), asthma and hair loss. Furthermore, the compounds of formula (I) are active as potassium channel activators which render them useful for treatment of peripheral vascular disease, hypertension, congestive heart failure, stroke, anxiety, cerebral anoxia and other neurodegenerative disorders. Thus, the present invention provides a method of treating smooth muscle disorders in mammals including man, which comprises administering to the afflicted mammal an effective amount of a compound or a pharmaceutical composition of the invention.

The present invention also provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

The compositions are preferably adapted for oral administration. However, they may be adapted for other modes of administration, for example, parenteral administration for a patient suffering from congestive heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with conventional excipients, such as a filler, a disintegrating agent , a binder, a lubricant, a flavoring agent and the like. They are formulated in conventional manner, for example, in a manner similar to that used for known antihypertensive agents, diuretics and β-blocking agents.

The following examples are presented to illustrate rather than limit the scope of the invention.

EXAMPLE 1

3-Butoxy-4-(1,2,2-trimethyl-2prolylamino)-cyclobut-3-ene-1,2-dione

Tetrahydrofuran (15 mL), 3,4-dibutoxy-3-cyclobutene-1,2-dione (2.26 g, 10 mmol) and 2-amino-3,3-dimethylbutane (1.01 g, 10 mmol) were stirred together for approximately 65 hours at room temperature. The waxy solid remaining after removal of solvent was dissolved in approximately 15 mL chloroform and chromatographed (flash, ethyl acetate/hexane) on silica. The appropriate fractions were freed of solvent to yield 2.41 g (95%) of a cream-colored waxy solid: mp 90°–9° C. (softens 85° C.).

Two recrystallization of 1.1 g of this material from hexane provided 0.833 g of the title compound as a white solid: mp 90°–93° C. (softens 88° C.); $^1$H NMR: (DMSO-d$_6$): δ 8.73 and 8.50 (two br d, 1H, rotamers), 4.64 (m, 2H), 3.92 and 3.41 (two m, 1H, rotamers), 1.71 (m, 2H), 1.38 (m, 2H), 1.11 (m, 3H), 0.91 (t, 3H), 0.84 (m, 9H) ppm. IR (KBr): 3135, 1800, 1690 cm$^{-1}$; MS (m/z): 253 (M$^+$).

Elemental Analysis for $C_{14}H_{23}NO_3$; Calcd: C, 66.37; H, 9.15; N, 5.53. Found: C, 66.47; H, 9.20; N, 5.50.

EXAMPLE 2

3-(2,4-Dichlorobenzylamino)-4-(1,2,2-trimethylproylamino)-cyclobut-3-ene-1,2-dione Tetrahydrofuran (10 mL), 3-butoxy-4-(1,2,2-trimethyl-propylamino)-cyclobut-3-ene-1,2-dione (1.01 g, 3.99 mmol, Example 1) and 2,4-dichlorobenzylamine (0.70 g, 4.0 mmol) were stirred together at room temperature for 14 hours. Following removal of solvent, the residue was triturated with diethyl ether and dried. The off-white solid product was recrystallized twice from nitromethane to yield 0.408 g (29%) of the title compound as a white solid: mp 234°–235° C.; $^1$H NMR: (DMSO-d$_6$): δ 7.67 (m, br, 1H), 7.65 (m, br, 1H), 7.48 (m, 2H), 7.32 (m, br, 1H), 4.80 (m, 2H), 3.90 (m, 1H), 1.10 (d, 3H), 0.86 (s, 9H) ppm. IR (KBr): 3140, 1790, 1640 cm$^{-1}$; MS (m/z): 354/356/358. HPLC indicates a major component (99%).

Elemental Analysis for $C_{17}H_{20}Cl_2N_2O_2$; Calcd.: C, 57.47; H, 5.67; N, 7.88. Found: C, 57.02; H, 5.44; N, 7.75. C, 57.69; H, 5.69; N, 7.79.

EXAMPLE 3

3-Ethoxy-4-(1,2,2-trimethyl-propylamino)-cyclobut-3-ene-1,2-dione

A solution of 3,4-diethoxy-3-cyclobutene-1,2-dione (10 g, 59 mmol) and (R)-2-amino-3,3-dimethylbutane (353 mL of a 0.2M solution in absolute ethanol, 71 mmol) was stirred at room temperature for 24 hours. Another portion of (R)-2-amino-3,3-dimethylbutane (150 mL of a 0.2M solution in absolute ethanol, 30 mmol) was added and the resulting solution was stirred at room temperature for 24 hours. The slurry was filtered, and the filtrate concentrated under reduced pressure. The resulting solid was triturated with hexane:ethyl acetate (150:5 mL), then washed with hexane to give 9.78 g (74%) of (R)-3-ethoxy-4-(1,2,2-trimethyl-propylamino)-cyclobut-3-ene-1,2-dione as a white solid: $^1$H NMR: (DMSO-d$_6$): δ 8.72 and 8.50 (two d, 1H, rotamers), 4.65 (m, 2H), 3.90 and 3.42 (two m, 1H, rotamers), 1.37 and 1.35 (two overlapping t, 3H, rotamers), 1.10 (two overlapping d, 3H, rotamers), 0.85 and 0.84 (two s, 9H, rotamers) ppm. IR (KBr): 3150, 2950, 1800, 1700 cm$^{-1}$; MS (m/z): 225 (M$^+$).

Elemental Analysis for $C_{12}H_{19}NO_3$; Calcd: C, 63.98; H, 8.50; N, 6.22. Found: C, 64.33; H, 8.54; N, 6.52.

(S)-3-Ethoxy-4-(1,2,2-trimethyl-propylamino)-cyclobut-3-ene-1,2-dione is produced by the same method by substituting (S)-2-amino-3,3-dimethylbutane for the (R)-2-amino-3,3-dimethylbutane employed in the preceding paragraph.

EXAMPLE 4

3-(2,4-Dichloro-6-methyl-benzylamino)-4-(1,2,2-trimethyl-prolylamino)-cyclobut-3-ene-1,2-dione The product of Example 3 (0.2 g, 0.88 mmol) and 2,4-dichloro-6-methylbenzylamine (0.17 g, 0.89 mmol, containing approximately 5% of a compound which is regioisomeric with respect to the substitution on the aryl ring) were placed in absolute ethanol (4.4 mL) and dichloromethane (2 mL). The resulting clear solution was allowed to stand at room temperature for 4 days. The reaction mixture was diluted with acetonitrile (5 mL) and filtered, rinsed with acetonitrile, and dried to give 0.3 g of a solid. Trituation with 10% methanol in dichloromethane gave 0.21 g (63%) of (R)-3-(2,4-dichloro-6-methyl-benzylamino)-4-(1,2,2-trimethyl-propylamino)-cyclobut-3-ene-1,2-dione as a white solid, which contains approximately 5% of a compound which is regioisomeric with respect to substitution on the aryl ring: mp >300° C.; $[α]^{25}{}_D$ =+31.86° (7.7 mg/mL, DMSO); $^1$H NMR (DMSO-d$_6$) d 7.54 (d, 1H), 7.39 (d, 1H), 7.31 (m, 1H), 7.17 (m, 1H), 4.89 (m, 2H), 4.70 (doublet of m, minor isomer), 3.89 (m, 1H), 2.41 (s, 3H), 2.31 (s, minor isomer), 1.09 (d, 3H), 0.85 (s, 9H) ppm. IR (KBr): 3150, 2950, 1800 cm$^{-1}$; MS (m/z) 368/370/372 (M$^+$).

Elemental analysis for $C_{18}H_{22}Cl_2N_2O_2$; Calc'd: C, 58.54; H, 6.01; N, 7.59. Found: C, 58.48; H, 6.02; N, 7.45.

(S)-3-(2,4-Dichloro-6-methyl-benzylamino)-4-(1,2,2-trimethyl-propylamino)-cyclobut-3-ene-1,2-dione is produced by the same method by substituting (S)-3-ethoxy-4-(1,2,2-trimethyl-propylamino)-cyclobut-3-ene-1,2-dione for the (R)-3-ethoxy-4-(1,2,2-trimethyl-propylamino)-cyclobut-3-ene-1,2-dione employed in the preceding paragraph.

EXAMPLE 5

3-Butoxy-4-(1,1-dimethyl-2propylamino)-cyclobut-3-ene-1,2-dione

A solution of 3,4-dibutoxy-3-cyclobutene-1,2-dione (4.53 g, 20 mmol) and 1,1-dimethylpropylamine (1.74 g, 20 mmol) in tetrahydrofuran (20 mL) was stirred at room temperature for approximately 19.5 hours. The solvent was removed and the residue was chromatographed (gravity, chloroform/hexane) on neutral, activity III silica (150 g). The white solid isolated from the appropriate eluates was recrystallized from hexane to give 4.105 g (86%) of a white product: mp 56.5°–57.5° C. (softens 55.5° C.).

One gram of this material was recrystallized twice from hexane to provide 0.794 g of the title compound as a white solid: mp 56°–57° C. (softens 55° C.); $^1$H NMR (DMSO-d$_6$): δ 8.63 and 8.48 (two br s, 1H, rotamers), 4.67 (m, br, 2H), 1.67 (m, br, 4H), 1.39 (m, 2H), 1.26 (m, br, 6H), 0.91 (t, 3H), 0.78 (t, 3H) ppm. IR (KBr): 3170, 1790, 1700 cm$^{-1}$; MS (m/z): 239 (M$^+$).

Elemental Analysis for $C_{13}H_{21}NO_3$; Calcd: C, 65.24; H, 8.85; N, 5.85; Found: C, 65.12; H, 8.90; N, 5.77

EXAMPLE 6

3-(2,4-Dichlorobenzylamino)-4-(1,1-dimethylpropylamino)-cyclobut-3-ene-1,2-dione A solution of 3-butoxy-4-(1,1-dimethyl-propylamino)-cyclobut-3-ene-1,2-dione (7.18 g, 30 mmol, Example 5) and 2,4-dichlorobenzylamine (5.28 g, 30 mmol) in tetrahydrofuran (40 mL) was stirred at room temperature for 16 hours. The solvent was removed and the residue was triturated thoroughly with diethyl ether and dried to give 8.94 g of a crude product. Successive recrystallizations of this material from acetonitrile (charcoal), acetonitrile (twice), acetone (charcoal) and acetone (twice) afforded 4.08 g (40%) of the title compound as a white, electrostatic solid: mp 196°–197° C. (softens 188° C.); $^1$H NMR (DMSO-d$_6$): δ 7.81 (m, 1H), 7.68 (m, 1H), 7.48 (m, 3H), 4.81 (d, 2H), 1.67 (m, 2H), 1.31 (s, 6H), 0.82 (t, 3H) ppm. IR (KBr): 3210, 1790, 1645 cm$^{-1}$; MS (m/z) 340/342/344 (M$^+$). HPLC indicates a major component (99% ). Differential scanning calorimetry studies indicate that this material is a mixture of crystal forms.

Elemental Analysis for $C_{16}H_{18}Cl_2N_2O_2$; Calcd: C, 56.32; H, 5.32; N, 8.21. Found: C, 55.93; H, 5.20; N, 8.18.

EXAMPLE 7

N-(2,4-Dichloro-benzyl)-N-[2-(1,1-dimethyl-prolylamino)-3,4-dioxo-cyclobut-1-enyl]-acetamide To the product of Example 6 (0.60g, 1.26 mmol) in a mixture of tetrahydrofuran (8 mL) and dimethylformamide (2 mL) at ambient temperature under a nitrogen atmosphere was added NaH (0.077 g of a 60% dispersion in mineral oil, 1.94 mmol). After stirring for 15 minutes at ambient temperature, acetic anhydride (0.183 mL, 1.94 mmol) was added neat. The mixture was stirred for 2 hours and was then diluted with brine and extracted with ethyl acetate (3×50 mL). The organic phase was washed with 10% aqueous $Na_2CO_3$ and brine, dried (MgSO$_4$), decolorized (charcoal), and concentrated to afford a residue. Crystallization from diethyl ether afforded 0.36 g (53%) of N-(2,4-dichloro-benzyl)-N-[2-(1,1-dimethyl-propylamino)-3,4-dioxo-cyclobut-1-enyl]-acetamide as a white solid, mp: 114°–116° C.; $^1$H NMR δ (DMSO-d$_6$) 7.66 (d, 1H), 7.32 (dd, 1H), 7.29 (d, 1H), 5.20 (br s, 2H), 2.15 (s, 3H), 1.70 (q, 2H), 1.35 (s, 6H), 0.85 (t, 3H) ppm. IR (KBr): 3400, 3300, 2950, 1800, 1700, 1580 cm$^{-1}$. MS (m/z) 382/384/386 (M$^+$).

Elemental analysis for $C_{18}H_{20}Cl_2N_2O_3$; Calc'd: C, 56.41; H, 5.26; N, 7.31. Found: C, 56.30; H, 5.27; N, 7.25.

EXAMPLE 8

N-(2,4-Dichloro-benzyl)-N-[2-(1,1-dimethyl-propylamino)-3,4-dioxo-cyclobut-1-enyl]-butyramide To the product of Example 6 (0.60g, 1.26 mmol) in a mixture of tetrahydrofuran (8 mL) and dimethylformamide (2 mL) at ambient temperature under a nitrogen atmosphere was added NaH (0.077 g of a 60% dispersion in mineral oil, 1.94 mmol). After stirring for 15 minutes at ambient temperature, butyric anhydride (0.317 mL, 1.94 mmol) was added neat. The mixture was stirred for 2 hours and was then diluted with brine and extracted with ethyl acetate (3×50 mL). The organic phase was washed with 10% aqueous $Na_2CO_3$ and brine, dried (MgSO4), decolorized (charcoal), and concentrated to afford a clear oil. Crystallization from diethyl ether afforded 0.52 g (72%) of N-(2,4-dichloro-benzyl)-N-[2-(1,1-dimethyl-propylamino)-3,4-dioxo-cyclobut-1-enyl]-butyramide as a white solid, mp: 112°–117° C.; $^1$H NMR δ (DMSO-d$_6$) 7.65 (d, 1H), 7.43 (dd, 1H), 7.29 (d, 1H), 5.16 (br s, 2H), 2.42 (t, 2H), 1.72 (q, 2H), 1.54 (m, 2H), 1.35 (s, 6H), 0.83 (m, 6H) ppm. IR (KBr): 3400, 3300, 2950, 1800, 1725, 1580 cm$^{-1}$. MS (m/z) 410/412/414 (M$^+$).

Elemental analysis for $C_{20}H_{24}Cl_2N_2O_3$; Calc'd: C, 58.40; H, 5.88; N, 6.81. Found: C, 58.40; H, 5.84; N, 6.86.

EXAMPLE 9

3-(2,4-Dichloro-6-methyl-benzylamino)-4-(1,1-dimethyl-propylamino)-cyclobut-3-ene-1 2-dione This compound was prepared in a procedure similar to the one described in Example 4. From 3-ethoxy-4-(1,1-dimethyl-propylamino)-cyclobut-3-ene-1,2-dione (16.67 g, 79.0 mmol) and 2,4-dichloro-6-methylbenzylamine (15.02 g, 79.0 mmol) in absolute ethanol (395 mL) there was obtained after filtration a white solid, which was washed with diethyl ether/hexane and dried in vacuo. This yielded 25.7 g (92%) of the title compound as a white solid: mp 247.1°14 248.3° C.; $^1$H NMR (DMSO-d$_6$) δ 7.54 (d, 1H), 7.44 (br t, 1H), 7.39 (d, 1H), 7.31 (s, 1H), 4.90 (d, 2H), 2.40 (s, 3H), 1.66 (q, 2H), 1.28 (s, 6H), 0.80 (t, 3H) ppm. IR (KBr): 3200, 2980, 1800, 1650 cm$^{-1}$; MS (m/z) 354/356/358 (M$^+$). Analytical HPLC indicates a major component (99.9%).

Elemental analysis for $C_{17}H_{20}Cl_2N_2O_2$; Calc'd: C, 57.47; H, 5.67; N, 7.89. Found: C, 57.31; H, 5.50; N, 7.80.

EXAMPLE 10

3-Butoxy-4-tert-butylamino-cyclobut-3-ene-1,2-dione

A solution of 3,4-dibutoxy-3-cyclobutene-1,2-dione (11.31 g, 50 mmol) and tert-butylamine (3.66 g, 50 mmol)

in tetrahydrofuran (80 mL) was stirred at room temperature for 71 hours. The solvent was removed and a solution of the residue in chloroform was washed with water and dried (anhydrous $Na_2SO_4$). Removal of the solvent and chromatographic (gravity, chloroform/hexane) purification of the amber liquid residue on a column of neutral, activity III silica (350 g ) provided 9.83 g (87%) of a white solid product, mp 67.0°–68.5° C. Two recrystallizations of an aliquot (800 mg) afforded 551 mg of the title compound as a white solid: mp 68°–69° C. (softens 67° C.); $^1$H NMR (DMSO-$d_6$): δ 8.75 and 8.59 (two br s, 1H, rotamers), 4.66 (m, br, 2H), 1.72 (m, 2H), 1.40 (m, 2H), 1.31 (m, 9H), 0.91 (t, 3H) ppm. IR (KBr): 3140, 1780, 1700 cm$^{-1}$; MS (m/z) 225 (M$^+$).

Elemental Analysis for $C_{12}H_{19}NO_3$; Calcd: C, 63.98; H, 8.50; N, 6.22. Found: C, 64.13; H, 8.60; N, 6.24.

EXAMPLE 11

3-(t-Butylamino)-4-(2,4-dichlorobenzylamino)cyclobut-3-ene-1,2-dione

A solution of 3-butoxy-4-tert-butylamino-cyclobut-3-ene-1,2-dione (1.13 g, 5.0 mmol, Example 10) and 2,4-dichlorobenzyl amine (0.884 g, 5.0 mmol) in tetrahydrofuran (15 mL) was stirred at room temperature for 16.5 hours. Removal of solvent, thorough trituration of the residue with diethyl ether and drying gave 1.50 g of a solid. Two recrystallizations of the crude product from acetonitrile afforded 1.22 g (74%) of the title compound as a white solid: mp 229°–230° C. (dec.); $^1$H NMR (DMSO-$d_6$): δ 7.77 (m, 1H), 7.68 (m, 1H), 7.61 (s, br, 1H), 7.48 (m, 2H), 4.79 (d, 2H), 1.36 (s, 9H) ppm. IR (KBr): 3300, 3220, 1780, 1660 cm$^{-1}$; MS (m/z): 326/328/330 (M$^+$). HPLC indicates a major component (99.6%).

Elemental Analysis for $C_{15}H_{16}Cl_2N_2O_2$; Calcd: C, 55.06; H, 4.93; N, 8.56; Found: C, 54.86; H, 4.89; N, 8.48

EXAMPLE 12

3-tert-Butylamino-4-(2,4-dichloro-6-methyl-benzylaimino)-cyclobut-3-ene-1,2-dione This compound was prepared in a procedure similar to the one described in Example 4. From 3-ethoxy-4-tert-butylamino-cyclobut-3-ene-1,2-dione (0.22 g, 1.1 mmol) and 2,4-dichloro-6-methylbenzylamine (0.22 g, 1.2 mmol, containing approximately 5% of a compound which is regioisomeric with respect to the substitution on the aryl ring) in absolute ethanol (5.5 mL) there was obtained 0.34 g (89%) of 3-tert-butylamino-4-(2,4-dichloro-6-methyl-benzylamino)-cyclobut-3-ene-1,2-dione as a white solid, which contains approximately 5% of a compound which is regioisomeric with respect to substitution on the aryl ring: mp 264°–268° C.; $^1$H NMR (DMSO-$d_6$) δ 7.54 (d, 1H), 7.46 (s, 1H), 7.43 (br t, 1H), 7.39 (d, 1H), 4.89 (d, 2H), 4.72 (d, minor isomer), 2.40 (s, 3H), 2.31 (s, minor isomer), 1.34 (s, 9H) ppm. IR (KBr): 3200, 2950, 1800, 1650 cm$^{-1}$; MS (m/z) 340/342/344 (M$^+$).

Elemental analysis for $C_{16}H_{18}Cl_2N_2O_2$; Calc'd: C, 56.32; H, 5.32; N, 8.21. Found: C, 56.09; H, 5.28; N, 8.16.

EXAMPLE 13

3-Butoxy-4-1-ethyl-propylamino)-cyclobut-3-ene-1,2-dione

A solution of 3,4-dibutoxy-3-cyclobut-3-ene-1,2-dione (2.26 g, 10 mmol) and 1-ethylpropylamine (0.872 g, 10 mmol) in tetrahydrofuran (8 mL ) was stirred at room temperature for 2.5 hours. The residue remaining after removal of solvent was dissolved in chloroform and the solution was washed with water and dried (anhydrous $Na_2SO_4$). Removal of solvent gave a waxy solid that was chromatographed (flash, chloroform/hexane) on silica. The solid isolated from the appropriate fractions was recrystallized twice from hexane to yield 0.896 g (37%) of the title compound: mp 65°–66° C.; $^1$H NMR (DMSO-$d_6$): δ 8.63 and 8.40 (two d, 1H, rotamers), 4.64 (m, 2H), 3.74 and 3.30 (two m, 1H, rotamers), 1.71 (m, 2H), 1.54 (m, 2H), 1.39 (m, 4H), 0.90 (m, 3H), 0.82 (m, 6H) ppm. IR (KBr): 3140, 1790, 1720 cm$^{-1}$; MS (m/z) 239 (M+).

Elemental Analysis for $C_{13}H_{21}NO_3$; Calcd: C, 65.25; H, 8.85; N, 5.85.

Found: C, 65.37; H, 9.07; N, 5.87.

EXAMPLE 14

3-(3,4-Dichloro-benzylamino)-4-(1-ethyl-propylamino)-cyclobut-3-ene-1,2-dione

This compound was prepared in a manner similar to Example 6 using the appropriate starting materials, to afford 3-(3,4-dichloro-benzylamino)-4-(1-ethyl-propylamino)-cyclobut-3-ene-1,2-dione as a white solid: mp 268°–269° C.

EXAMPLE 15

3-(2,4-Dichloro-benzylamino)-4-(1-ethyl-propylamino-cyclobut-3-ene-1,2-dione

This compound was prepared in a manner similar to Example 6 using the appropriate starting materials to afford 3-(2,4-dichloro-benzylamino)-4-(1-ethyl-propylamino)-cyclobut-3-ene-1,2-dione as very pale yellow solid: mp 210°–211° C.

EXAMPLE 16

3-(2,4-Dichloro-6-methyl-benzylamino)-4-(2,2,3,3,3-pentaflouro-cyclobtut-3-ene-1,2-dione A solution of 3,4-diethoxy-3-cyclobutene-1,2-dione (4.2 mld, 28.4 mmol) and 2,2,3,3,3-pent afluoropropylaine (4.24 g, 28.4 snmol) in absolute ethanol (142 mL) was stirred at room temperature for 24 hours. The solution was concentrated under reduced pressure and triturated with 10% ethyl acetate in hexane to yield 1.14 g (14.6%) of a white solid,: mp 95°–100° C.; $^1$H NMR (DMSO-$d_6$) δ 9.40 and 9.20 (two br m, 3H, rotamers), 4.67 (q, 2H), 4.33 and 4.11 (two br t, 2H, rotamers), 1.36 (br m, 3H); MS (m/z) 274 ([M+H]$^+$). Following the procedure described in Example 4, from a portion of this solid, 3-ethoxy-4-(2,2,3,3,3-pentafluoro-propylamino)-cyclobut-3-ene-1,2-dione (0.72 g, 2.6 mmol) and 2,4-dichloro-6-methylbenzylamine (0.5 g, 2.6 mmol) there was obtained 1.03 g, (94%) of the title col pound as a white solid: mp 287°–292° C.; $^1$H NMR (DMSO-$d_6$) δ 7.62 (br m, 2H), 7.53 (s, 1H), 7.38 (d, 1H), 4.89 (d, 2H), 4.43 (doublet of t, 2H), 2.40 (s, 3H) ppm.

Elemental a nalysis for $C_{15}H_{11}Cl_2F_5N_2O_2$; Calc'd: C, 43.19; H, 2.66; N, 6.72. Found: C, 43.13; H, 2.61; N, 6.74.

EXAMPLE 17

N-(2,4-Dichloro-6-methyl-benzyl)-N-[2-(1,1-dimethyl-2proplylamino)-3,4-dioxo-cyclobut-1-envl]-butyramide To 3-(2,4-dichloro-6-methyl-benzylamino)-4i(1,1-dimethyl-propylamino)-cyclobut-3-ene-1,2-dione (0.50 g, 1.41 mmol) in N,N-dimethylformamide (2 mL) and tetrahydrofuran (8 mL) was added sodium hydride (0.062 g of a 60% dispersion in mineral oil, 1.54 mmmol) at 0° C. The frothy suspension was stirred for 1 hour as the mixture was warmed to 25° C. Butyric anhydride (0.24 g, 1.54 mmol) was added and the reaction mixture was stirred at 0° C. for 15 minutes and then allowed to warm to room temperature. After stirring overnight, the reaction mixture was poured into brine (50 mL) and extracted with ethyl acetate (3×50 mL). The organic layer was dried over magnesium sulfate and decolorized (charcoal). The solvent was removed in vacuo and the remaining oil was triturated with diethyl ether/petroleum ether to yield 0.31 g (53%) of a white solid: mp 117.2°–118.4° C.; $^1$H NMR (DMSO-$d_6$) δ 8.80 (br s, 1H), 7.39 (d, 1H), 7.28 (d, 1H), 5.06 (s, 2H), 2.34 (s, 3H), 2.29 (t, 2H), 1.67 (q, 2H), 1.51 (q, 2H), 1.30 (s, 6H), 0.82 (q, 6H) ppm. IR (KBr): 3230, 2950, 1800, 1744, 1700, 1570 cm$^{-1}$; MS (m/z) 424 (M$^+$).

Elemental analysis for $C_{21}H_{26}Cl_2N_2O_3$; Calc'd: C, 59.30; H, 6.16; N, 6.59. Found: C, 59.34; H, 6.09; N, 6.52.

EXAMPLE 18

N-(2,4-Dichloro-6-methyl-benzyl)-N-[2-(1,1-dimethyl-propylamino)-3,4-dioxo-cyclobut-1-enyl]-acetamide This compound was prepared according to the procedure described in Example 17. From 3-(2,4-dichloro-6-methyl-benzylamino)-4-(1,1-dimethyl-propylamino)-cyclobut-3-ene-1,2-dione (0.50 g, 1.41 mmol) and acetic anhydride (0.16 g, 1.54 mmol) there was obtained 0.36 g (64%) of the title compound as a white solid: mp 112.2°–113.9° C.; $^1$H NMR (DMSO-$d_6$) δ 8.71 (br s, 1H), 7.40 (d, 1H), 7.29 (d, 1H), 5.06 (s, 2H), 2.35 (s, 2H), 2.05 (s, 3H), 1.67 (q, 2H), 1.30 (s, 6H), 0.81 (t, 3H) ppm. IR (KBr): 3230, 2950, 1800, 1755, 1590 cm$^{-1}$; MS (m/z) 396 (M$^+$).

Elemental analysis for $C_{19}H_{22}Cl_2N_2O_3$; Calc'd: C, 57.44; H, 5.58; N, 7.05. Found: C, 57.16; H, 5.52; N, 6.94.

EXAMPLE 19

N-(tert-butyl)-N-[2-(2,4-Dichloro-6-methyl-benzylamino)-3,4-dioxo-cylobut-1-enyl]-propionamide To 3-butoxy-4-tert-butylamino-cyclobut-3-ene-1,2-dione (0.50 g, 2.5 mmol) in tetrahydrofuran (12.6 mL) was added sodium hydride (0.091 g of a 80% dispersion in mineral oil, 3.0 mmol). The suspension was stirred for 20 minutes at room temperature. The slightly cloudy yellow solution was concentrated under reduced pressure, and the resulting white solid was suspended in propionic anhydride (2 mL) and dichloromethane (3 mL). The reaction mixture was stirred at room temperature for 18 hours, then heated at 115° C. for 24 hours. After standing at room temperature for 5 days the reaction mixture was diluted with dichloromethane, filtered, and concentrated under reduced pressure. Purification by column chromatography (silica gel, hexane/ethyl acetate) gave 0.09 g of material that was placed in acetonitrile (1.8 mL). 2,4-Dichloro-6-methylbenzylamine (67 mg, 0.35 mmol) and acetonitrile (2 mL) was added. After 3 days at room temperature, the reaction mixture was concentrated under reduced pressure, and the resulting solid was recrystallized from hexane and ethyl acetate to give 74 mg (53%) of a white solid: mp 177°–180° C.; $^1$H NMR (DMSO-$d_6$) δ 9.31 (t, 1H), 7.54 (d, 1H), 7.40 (d, 1H), 4.94 (d, 2H), 2.40 (s, 3H), 2.09 (q, 2H), 1.37 (s, 9H), 0.87 (t, 3H) ppm.

Elemental analysis for $C_{19}H_{22}Cl_2N_2O_3$; Calc'd: C, 57.44; H, 5.58; N, 7.05. Found: C, 56.41; H, 5.19; N, 6.98.

EXAMPLE 20

3-(2,4-dichloro-6-methyl-benzylamino)-4-(1,2-dimethyl-2-fluoro-propylamino)-cyclobut-3-ene-1,2-dione Step 1) 3-Fluorovalinol To a solution of lithium borohydride (1.61 g, 74 mmol) in THF(40 mL) under a nitrogen atmosphere was added trimethylsilyl chloride(18.8 mL, 14.8 mmol) via pipet. A precipitate quickly formed. After 3 minutes, 3-fluorovaline (5 g, 37 mmol) was added in three portions. This mixture was stirred for 24 hours. The reaction was quenched by the dropwise addition of methanol. The methanol and THF were removed on a rotary evaporator (30 degree water bath) and water (25 mL) was added. The aqueous mixture was made basic with 2.5N aq. NaOH and was then extracted with dichloromethane (4×50 mL). The combined organics were dried($Na_2SO_4$), filtered and evaporated to give 3.83 g of 3-fluorovalinol: $^1$H NMR (CDCl$_3$) δ 3.71 (dd, 1H), 3.36 (m, 1H), 2.90 (m,1H), 2.10 (br, 2H), 1.38 (d, 3H), 1.33 (d, 3H) ppm Step 2) N-Butoxycarbonyl-3-fluorovalinol To a solution of 3-fluorovalinol (3.79 g, 31.4 mmol) in chloroform (35 mL) under a nitrogen atmosphere was added a solution of di-t-butyl dicarbonate (6.84 g, 31.4 mmol) in chloroform (15 mL). The mixture was stirred at room temperature for four hours, then the solvent was removed on a rotary evaporator. The residue was dissolved in diethyl ether (100 mL), washed with 20% phosphoric acid (1×50 mL), brine (1×50 mL), saturated aqueous sodium bicarbonate (1×50 mL), brine (1×50 mL), and then dried(MgSO$_4$). Filtration and concentration under reduced pressure gave 6.34 g of N-butoxycarbonyl-3-fluorovalinol as a white solid: $^1$H NMR (CDCl$_3$) δ 5.08 (br, 1H), 3.82 (m, 2H), 3.68 (m, 1H), 1.46 (s, 9H), and 1.39 (d, 3H) ppm.

Step 3) N-Butoxycarbonyl-1-iodo-2-amino-3-fluoro-3-methyl-n-butane

To a well-stirred mixture of polystyryl supported triphenyl phosphine (29.3 mmol) in dry dichloromethane (40 mL) under a nitrogen atmosphere was added iodine (7.44 g, 29.3 mmol). After ten minutes, imidazole (2.0 g, 29.3 mmol) was added followed in ten minutes by a solution of N-butoxycarbonyl-3-fluorovalinol (13.3 mmol) in dichloromethane (200 mL). The mixture was heated to reflux for two hours. The cooled mixture was filtered through Celiteo® and the filtrate was evaporated. The residue was dissolved in diethyl ether (150 ML) and this solution was washed with dilute aqueous sodium thiosulfate (1×75 mL) and water (2×75 mL). The organic layer was dried (Na$_2$SO$_4$), filtered through a pad of silica gel and evaporated to afford 3.46 grams of N-butoxycarbonyl-1-iodo-2-amino-3-fluoro-3-methyl-n-butane: $^1$H NMR (CDCl$_3$) δ 4.72 (br d, 1H), 3.86 (br m, 1H), 3.56 (dd, 1H), 1.47 (s, 9H), 1.43 (m, 6H) ppm.

Step 4) N-Butoxycarbonyl-2-amino-3-fluoro-3-methyl-n-butane

A Parr bottle was charged with palladium (II) hydroxide (800 mg), a solution of N-butoxycarbonyl-1-iodo-2-amino-3-fluoro-3-methyl-n-butane (3.26 g, 9.8 mmol) in ethanol (80 mL) and triethylamine (0.99 g, 9.8 mmol). The reaction mixture was placed under hydrogen gas (50 psig) and shaken for 20 hours. The mixture was filtered through celite and evaporated. The residue was dissolved in diethyl ether (100 mL) and washed with 1N aq. HCl (2×50 mL), water (2×50 mL), and then dried (MgSO$_4$). Filtration and evaporation gave a residue that was chromatographed (silica gel, diethyl ether/hexane (3/1)) to afford 1.80 g of N-butoxycarbonyl-2-amino-3-fluoro-3-methyl-n-butane: $^1$H NMR (CDCl$_3$) δ 4.65 (br, 1H), 3.70 (br m, 1H), 1.45 (s, 9H), 1.39 (d, 3H), 1.32 (d, 3H) and 1.18 (d, 3H) ppm.

Step 5) 3-Ethoxy-4-(3-fluoro-3-methyl-n-butyl-2-amino)-3-cyclobutene-1,2-dione

A mixture of N-butoxycarbonyl-2-amino-3-fluoro-3-methyl-n-butane (1.75 g, 8.5 mmol), dichloromethane (5 mL), trifluoroacetic acid (4 mL), and methanol (0.75 mL) was warmed to 45° C. for five hours. The volatile components were removed on a rotary evaporator and the syrupy residue was used without further purification. To a solution of 3-fluoro-3-methyl-n-butyl-2-amine trifluoroacetate salt (8.5 mmol) in ethanol (42.5 mL) was added 3,4-diethoxy-3-cyclobutene-1,2-dione (1.44 g, 8.5 mmol) followed by triethylamine (2.58 g, 25.5 mmol). The reaction mixture was stirred under a nitrogen atmosphere at room temperature for two hours then the temperature was raised to 50° C. for five hours. The mixture was cooled and the solvents removed on a rotary evaporator. The residue was dissolved in diethyl ether (90 mL) and washed with water (1×60 mL), 1 N aq. HCl (1×60 mL), water 1×60 mL). The organic layer was dried (MgSO$_4$), filtered, and evaporated. The residue was chromatographed (silica gel, diethyl ether) to afford 1.65 g of 3-ethoxy-4-(3-fluoro-3-methyl-n-butyl-2-amino)-3-cyclobutene-1,2-dione as a white solid: $^1$H NMR (CDCl$_3$) δ 6.21 (br, 1H), 4.77 (br m, 2H), 3.80 (br, 1H), 1.47 (t, 3H), 1.43 (d, 3H), 1.36 (d, 3H) and 1.32 (d, 3H) ppm.

Step 6) 3-(2,4-dichloro-6-methyl-benzylamino)-4-(1,2-dimethyl-2-fluoro-propylamino)-cyclobut-3-ene-1,2-dione To a solution of 3-ethoxy-4-(3-fluoro-3-methyl-n-butyl-2-amino)-3-cyclobutene-1,2-dione (0.573 g, 2.5 mmol) in dry THF (8 mL) was added 2,4-dichloro-6-methylbenzylamine (0.523 g, 2.75 mmol). The mixture was heated to 70° C. under a nitrogen atmosphere for 18 hours. The mixture was cooled to room temperature with stirring and vacuum filtered through a fritted glass filter. The solid was washed well with several portions of an ethanol/diethyl ether (1/1) solvent mixture. The solid was air dried then heated to 77° C. under high vacuum for 16 hours. This afforded 0.48 g of the title compound as a white solid: 1H NMR (DMSO-d$_6$) δ 7.54 (s, 1H), 7.40 (br, 1H), 7.38 (s, 2H), 4.90 (m, 2H), 4.17 (br, 1H), 2.41 (s, 3H), 1.32 (d, 3H), 1.27 (d, 3H), 1.18 (d, 3H), ppm. IR (KBr): 1850 cm$^{-1}$; MS (m/z) 373 ([M+H]$^+$).

EXAMPLE 21

3-Butoxy-4-(2,4-dichlorobenzylamino)-cyclobut-3-ene-1,2-dione

A solution of 3,4-dibutoxy-3-cyclobutene-1,2-dione (3.39 g, 15 mmol) and 2,4-dichlorobenzylamine (2.64 g, 15 mmol) in tetrahydrofuran (20 mL) was stirred at room temperature for 5.5 hours. After removal of solvent, the residue was dissolved in chloroform (approximately 30 mL) and chromatographed (flash, ethyl acetate/hexane) on silica. The appropriate fractions were freed of solvent to give 4.31 g (88%) of a white product: mp 140°–142° C. (softens 137° C.). Three recrystallizations of 1.1 g of this material from methyl t-butyl ether provided 0.566 g of the title compound as a white solid: mp 139.5°–140.0° C. (softens 137.5° C.; $^1$H NMR (DMSO-d$_6$) δ 9.25 and 9.00 (two m, 1H, rotamers), 7.64 (d, 1H), 7.51°–7.34 (m, 2H), 4.69 (m, 2H), 4.56 (s, 2H), 1.72 (m, 1H), 1.58 (m, 1H), 1.38 (m, 1H), 1.19 (m, 1H), 0.19 and 0.82 (two t, 3H, rotamers) ppm. IR (KBr): 3160, 1760, 1700 cm$^{-1}$. MS (m/z) 327/329/331 (M$^+$). HPLC indicates a major component (>99%).

Elemental analysis for C$_{15}$H$_{15}$Cl$_2$NO$_3$; Calc'd: C, 54.90; H, 4.61; N, 4.27. Found: C, 54.98; H, 4.51; N, 4.11.

EXAMPLE 22

3-(2,4-Dichlorobenzylamino)-4-(2-hydroxy-1,1-dimethylethylamino)-cyclobut-3-ene-1,2-dione Tetrahydrofuran (10 mL), 3-butoxy-4-(2,4-dichlorobenzylamino)-cyclobut-3-ene-1,2-dione (1.31 g, 3.94 mmol, Example 21), and 2-amino-2-methyl-1-propanol (0.36 g, 4.0 mmol) were stirred together for 43.5 hours at room temperature. Following removal of solvent, the residue was triturated with diethyl ether and dried to yield 1.13 g of a yellow solid. Three recrystallizations of the crude product from methanol gave 0.503 g of the title compound as cream-colored solid: mp 237°–238° C. (softens 234° C.); $^1$H NMR (DMSO-d$_6$) δ 7.94 (t, 1H), 7.68 (m, 1H), 7.54 (m, 1H), 7.48 (m, 2H), 5.04 (t, 1H), 4.79 (d, 2H), 3.39 (d, 2H), 1.15 (s, 6H) ppm. IR (KBr): 3380, 3250, 1780, 1650 cm$^{-1}$. MS (m/z) 343 ([M+H]$^+$). HPLC indicates a major component (99.9%).

Elemental analysis for C$_{15}$H$_{16}$Cl$_2$N$_2$O$_3$; Calc'd: C, 52.49; H, 4.70; N, 8.16. Found: C, 52.57; H, 4.59; N, 8.12.

EXAMPLE 23

3-(2,4-Dichlorobenzylamino)-4-(1,2,2-trimethylpropylamino)-cyclobut-3-ene-1,2-dione The product of Example 3 (0.901 g, 4.0 mmol) and 2,4-dichlorobenzylamine (0.704 g, 4.0 mmol) in tetrahydrofuran (20 mL) were stirred at room temperature for approximately 16 hours and then were refluxed for approximately 24 hours. After removal of solvent, the residue was recrystallized from methanol (charcoal) and again recrystallized from methanol to afford 0.25 g (18%) of (R)-3-(2,4-dichlorobenzylamino)-4-(1,2,2-trimethylpropylamino)-cyclobut-3-ene-1,2-dione as a white solid: mp 235°–239° C. (softens 233° C.); [α]$^{25}_D$ =+26.28° (9.58 mg/mL, DMSO); $^1$H NMR (DMSO-d$_6$) δ 7.67 (s, 1H), 7.63 (br s, 1H), 7.48 (m, 2H), 7.30 and 7.15 (two br d, 1H, rotamers), 4.80 (m, 2H), 3.90 (br s, 1H), 1.10 (m, 3H), 0.86 (m, 9H) ppm. IR (KBr): 3180, 1800, 1650 cm$^{-1}$. MS (m/z) 354/356/358 (M$^+$). Analytical HPLC indicates chemical purity (96%) and optical purity (100%).

Elemental analysis for C$_{17}$H$_{20}$Cl$_2$N$_2$O$_3$; Calc'd: C, 57.48; H, 5.68; N, 7.89. Found: C, 57.96; H, 5.86; N, 7.77. C, 58.11; H, 5.76; N, 8.05.

(S)-3-(2,4-Dichlorobenzylamino)-4-(1,2,2-trimethylpropylarnino)-cyclobut-3-ene-1,2-dione is produced by the same method by substituting (S)-3-ethoxy-4-(1,2,2-trimethyl-propylamino)-cyclobut-3-ene-1,2-dione for the (R)-3-ethoxy-4-(1,2,2-trimethyl-propylamino)-cyclobut-3-ene-1,2-dione employed in the preceding paragraph.

EXAMPLE 24

3-tert-Butylamino-4-(3,4-dichlorobenzylamino)-cyclobut-3-ene-1,2-dione

A solution of 3-butoxy-4-tert-butylamino-cyclobut-3-ene-1,2-dione (1.13 g, 5 mmol, Example 10) and 3,4-dichlorobenzylamine (0.880 g, 5.0 mmol) in tetrahydrofuran (15 mL) was stirred at room temperature for approximately 96 hours. The residue isolated after removal of solvent was recrystallized from N,N-dimethylformamide (twice) and from 2-methoxyethanol to provide 0.687 g (42%) of the title compound as a white solid: mp 302°–303° C.; $^1$H NMR (DMSO-d$_6$) δ 7.77 (m, 1H), 7.65 (d, 1H), 7.62 (d, 1H), 7.55 (s, 1H), 7.33 (m, 1H), 4.71 (d, 2H), 1.35 (s, 9H) ppm. IR (KBr): 3450, 3230, 1800, 1650 cm$^{-1}$. MS (m/z) 326/328/330 (M$^+$). HPLC indicates a major component (>99%).

Elemental analysis for C$_{15}$H$_{16}$Cl$_2$N$_2$O$_2$; Calc'd: C, 55.06; H, 4.93; N, 8.56. Found: C, 54.81; H, 4.56; N, 8.44.

EXAMPLE 25

3-(3,4-Dichlorobenzylamino)-4-(1,1-dimethylpropylamino-cyclobut-3-ene-1,2-dione

Tetrahydrofuran (15 mL), 3-butoxy-4-(1,1-dimethylpropylamino)-cyclobut-3-ene-1,2-dione (1.20 g, 5.0 mmol) and 3,4-dichlorobenzylamine (0.88 g, 5.0 mmol) were stirred together at room temperature for approximately 16 hours. Removal of solvent gave 1.67 g of a white solid which was recrystallized from methanol (twice) to yield 1.06 g (62%) of the title compound as a white solid: mp 277°–279° C.; $^1$H NMR (DMSO-d$_6$) δ 7.80 (m, 1H), 7.65 (d, 1H), 7.62 (d, 1H), 7.42 (s, 1H), 7.34 (m, 1H), 4.73 (d, 2H), 1.66 (m, 2H), 1.30 (s, 6H), 0.81 (t, 3H) ppm. IR (KBr): 3300, 3240, 1790, 1650 cm$^{-1}$. MS (m/z) 340/342/344 (M$^+$). HPLC indicates a major component (98.9%).

Elemental analysis for C$_{16}$H$_{18}$Cl$_2$N$_2$O$_2$; Calc'd: C, 56.32; H, 5.32; N, 8.21. Found: C, 56.34; H, 5.03; N, 8.03.

EXAMPLE 26

(2,4-Dichloro-6-methyl-benzyl)-[2-(1,1-dimethyl-propylamino)-3,4-dioxo-cyelobut-1-enyl]-carbamic acid tert-butyl ester Step 1) Preparation of (2,4-dichloro-6-methyl-benzyl)-[2-butoxy-3,4-dioxo-cyclobut-1-enyl]-carbamic acid tert-butyl ester To 2,4-dichloro-6-methylbenzylamine (2.0 g, 10.5 mmol) in tetrahydrofuran (15 mL) was added 3,4-dibutoxy-3-cyclobutene-1,2-dione (2.85 g, 12.6 mmol). The mixture was stirred at room temperature under nitrogen for 24 h. The reaction mixture was concentrated under reduced pressure and the resulting residue was recrystallized from a mixture of ethyl acetate and hexane. The solid was filtered and dried. This gave 3.15 g (84%) of a solid, which was used without further purification. A portion of this solid, 3-(2,4-dichloro-6-methyl-benzylamino)-4-butoxy-cyclobut-3-ene-1,2-dione, (1.12 g, 3.1 mmol) in dichloromethane (20 mL) was mixed with triethylamine (0.44 mL, 3.1 mmol), di-tert-butyl dicarbonate (1.45 g, 6.6 mmol), and 4-dimethylaminopyridine (0.38 g, 3.1 mmol). The reaction mixture was stirred at room temperature under nitrogen for 24 h. The resulting solution was filtered through a plug of silica gel, which was subsequently washed with a solution of 1:1 hexane:ethyl acetate (100 mL). The filtrate was concentrated under reduced pressure to give 1.25 g (86%) of a solid: $^1$H NMR (DMSO-d$_6$) δ 7.43 (s, 1H), 7.32 (s, 1H), 5.10 (s, 2H), 4.74 (t, 2H), 2.38 (s, 3H), 1.71 (m, 2H), 1.40°–1.29 (m overlappping a singlet at δ 1.31, 11H), 0.89 (t, 3H).

Step 2) (2,4-Dichloro-6-methyl-benzyl)-[2-(1,1 -dimethyl-propylamino)-3,4-dioxo-cyclobut-1-enyl]-carbamic acid tert-butyl ester The product from Example 26, Step 1 (1.20 g, 2.63 mmol) was dissolved in tetrahydrofuran 30 mL). 1,1-Dimethylpropylamine (0.62 mL, 5.3 mmol) was added. The reaction mixture was stirred at room temperature under nitrogen for 3 days. The solvent was removed under reduced pressure, and the resulting yellow oil was triturated with diethyl ether and hexane to give 1.15 g (95%) of the title compound as a white solid: mp 141.2°–142.5° C.; $^1$H NMR (DMSO-d$_6$) δ 7.94 (br s, 1H), 7.46 (d, 1H), 7.34 (d, 1H), 5.25 (s, 2H), 2.36 (s, 3H), 1.71 (q, 2H), 1.35 (s, 6H), 1.25 (s, 9H), 0.85 (t, 3H). MS (m/z) 454/456/458 (M$^+$).

Elemental analysis for C$_{22}$H$_{28}$Cl$_2$N$_2$O$_4$ Calc'd: C, 58.03; H, 6.20; N, 6.15. Found: C, 58.09; H, 6.11; N, 6.09.

The smooth muscle relaxing activity of the compounds of this invention was established in accordance with standard pharmaceutically accepted test procedures with representative compounds as follows:

Sprague-Dawley rats (150–200 g) are rendered unconscious by $CO_2$ asphyxiation and then euthanized by cervical dislocation. The bladder is removed into warm (37 deg.C.) physiological salt solution (PSS) of the following composition (mM): NaCl, 118.4; KCl, 4.7; CaCl$_2$, 2.5; MgSO$_4$, 4.7; H$_2$O, 1.2; NaHCO$_3$, 24.9; KH$_2$PO$_4$, 1.2; glucose, 11.1; EDTA, 0.023; gassed with 95% O$_2$; ⅖% CO$_2$; pH 7.4. The bladder is opened and then cut into strips 1–2 mm in width and 7–10 mm in length. The strips are subsequently suspended in a 10 mL tissue bath under an initial resting tension of 1.5 g. The strips are held in place by two surgical clips one of which is attached to a fixed hook while the other is attached to an isometric force transducer. The preparations, which usually exhibit small spontaneous contractions, are allowed to recover for a period of 1 hour prior to a challenge with 0.1 µM carbachol. The carbachol is then washed out and the tissue allowed to relax to its resting level of activity. Following a further 30 minute period of recovery an additional 15 mM KCl are introduced into the tissue bath. This increase in KCl concentration results in a large increase in the amplitude of spontaneous contractions (and initiation of contractions in previously quiescent strips) superimposed upon a small increase in basal tone. Following stabilization of this enhanced level of contractile activity, incremental increases in the concentration of test compound or vehicle are introduced into the tissue bath. Contractile activity is measured for each compound or vehicle concentration during the last minute of a 30 minute challenge.

The isometric force developed by the bladder strips is measured using a concentration required to elicit 50% inhibition of pre-drug contractile activity. The (IC$_{50}$ concentration) is calculated from this concentration-response curve. The maximum percentage inhibition of contractile activity evoked by a test compound is also recorded for concentrations of test compound less than or equal to 30 µM.

The results of this study are shown in Table I.

TABLE I

Inhibition of Contractions in Isolated Rat Bladder Strips

| Compound | n | IC$_{50}$ (µM) |
| --- | --- | --- |
| Example 2 | 4 | 2.0 ± 1.0 |
| Example 4 | 4 | 9.8 ± 5.1 |
| Example 6 | 2 | 0.11 ± 0.002 |
| Example 7 | 2 | 15.8 ± 0.05 |
| Example 8 | 2 | C$^b$ = 82.8 ± 26.0% |
|  | 1 | I$^a$ = 10.2% |
| Example 9 | 8 | 0.20 ± 0.06 |
| Example 11 | 4 | 1.3 ± 0.6 |
| Example 12 | 2 | 0.22 ± 0.08 |
| Example 14 | 4 | I$^a$ = 22 ± 5.9% |
| Example 15 | 6 | 2.0 ± 0.8 |
| Example 16 | 2 | 9.35 ± 0.46 |
|  | 4 | I$^a$ = 36 ± 3.2% |
| Example 17 | 2 | C$^b$ = 245 ± 15% |
| Example 18 | 3 | I$^a$ = 26 ± 13.8% |
| Example 19 | 2 | C$^b$ = 92.5 ± 44.2% |

TABLE I-continued

Inhibition of Contractions in Isolated Rat Bladder Strips

| Compound | n | $IC_{50}$ (µM) |
|---|---|---|
| Example 20 | 2 | 2.53 ± 0.19 |
| Example 22 | 2 | 24.0 ± 9.3 |
| Example 23 | 2 | 0.34 ± 0.22 |
| Example 24 | 4 | 1.48 ± 0.57 |
|  | 3 | $I^a$ = 32.5 ± 3.1% |
|  | 1 | $C^b$ = 30% |
| Example 25 | 4 | 8.9 ± 4.0 |
|  | 2 | $C^b$ = 57.9 ± 4.2% |
| Example 26 | 3 | 4.5 ± 4.2 |

[a]Percent inhibition at 30 µM
[b]Percent contraction at 30 µM

In addition, we tested the ability of compounds to inhibit the hyperactivity of hypertrophied bladder (detrussor) smooth muscle in conscious female rats with hypertrophied bladders and thereby alleviate urinary incontinence in rats according to the following protocol described by Malmgren et al., *J. Urol.* 142:1134, 1989:

Female Sprague-Dawley rats, ranging in weight from 190–210 g are used. Up to 25 animals are prepared each time. After developemnt of bladder hypertrophy 4–8 animals are used per test.

Compounds are dissolved in PEG-200 and administered by gastric gavage or intraveneously in a volume of 5 ml/kg. For primary screening all drugs are administered at the arbitrary dose of 10 mg/kg p.o. to groups of 4 rats.

The animals are anesthetized with halothane. Through a midline incision the bladder and urethra are exposed and a ligature of 4-0 silk is tied around the proximal urethra in the presence of a stainless steel rod (1 mm diameter) to produce a partial occlusion. The rod is then removed. The abdominal region is closed using surgical staples and each rat receives 150,000 units of bicillin C-R. The animals are allowed six weeks to develop sufficient bladder hypertrophy. After six weeks, the ligature is removed under halothane anesthesia and a catheter (PE 60) with a cuff is placed in the dome of the bladder and secured with a purse string suture. The catheter is tunneled under the skin and exteriorized through an opening in the back of the neck. The abdominal incision is sutured and the free end of the catheter sealed. In order to prevent infections the rats receive an injection of bicillin C-R (150000 units/rat). Two days later the animals are used in cystometrical evaluations. The animals are placed in the metabolic cages and the catheter is attached (using a "T" connector) to a Statham pressure transducer (Model P23Db) and to a Harvard infusion pump. A plastic beaker attached to a force displacement transducer (Grass FTO3) is placed under the rat's cage to collect and record urine volume. Animals are allowed 15–30 minutes to rest before the saline infusion (20 ml/hr for 20 minutes) is started for the first cystometry period. Two hours after the first cystometry period, the rats are dosed with the vehicle or the test compound and one hour later a second cystometry is performed.

The following urodynamic variables are recorded:

| | |
|---|---|
| Basal bladder pressure = | the lowest bladder pressure during cystometry |
| Threshold pressure = | bladder pressure immediately prior to micturition |
| Micturition volume = | volume expelled |
| Micturition pressure = | peak pressure during voiding |
| Spontaneous activity = | mean amplitude of bladder pressure fluctuations during filling |

Presentation of results:

The mean value of each variable is calculated before and after compound administration. For each compound the changes in the variables measured are compared to the values obtained before treatment and expressed as percent inhibition. The data are also subjected to 2-way analysis of variance to determine significant (p<0.05) changes in the variable measured. The most characteristic finding in this rat model is spontaneous bladder contractions which develop during filling.

The results of this study are shown in Table II.

TABLE II

Inhibition of Spontaneous Contractions In Vivo

| Compound | # of animals | dose mg/kg (p.o.) | % Red $(F)^c$ |
|---|---|---|---|
| Example 6 | 7 | 1 mg/kg | $-40 ± 13^d$ |
|  | 10 | 3 mg/kg | $-58 ± 9^d$ |
|  | 7 | 10 mg/kg | $-68 ± 10^d$ |
| Example 9 | 6 | 1 mg/kg | -63 ± 13 |
|  | 4 | 3 mg/kg | -82 ± 5 |
| Example 12 | 3 | 3 mg/kg | -53 ± 18 |
| Example 17 | 2 | 10 mg/kg | -87 ± 2 |

[c]Percent reduction in the total number of spontaneous contractions in the hypertrophied rat bladder model
[d]Findings obtained on a prior lot of this compound, mp. 195–196° C., $IC_{50}$ = 0.21 ± 0.04 µM(n = 4)

Hence, the compounds of this invention have a pronounced effect on smooth muscle contractility and are useful in the treatment of urinary incontinence, irritable bladder and bowel disease, asthma, hypertension, stroke, and similar diseases as mentioned above, which are amenable to treatment with potassium channel activating compounds by administration, orally parenterally, or by aspiration to a patient in need thereof.

What is claimed is:

1. A compound of the formula

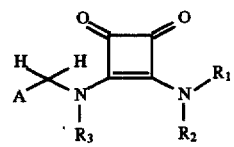

(I)

wherein:

$R_1$ is straight chain alkyl of 1 to 10 carbon atoms, branched chain alkyl of 3 to 10 carbon atoms, cycloalkyl of 3 to 10 carbon atoms, hydroxyalkyl of 2 to 10 carbon atoms, fluoroalkyl of 1 to 10 carbon atoms or polyfluoroalkyl of 1 to 10 carbon atoms;

$R_2$ and $R_3$ are, independently, hydrogen or an acyl substituent selected from the group consisting of formyl, alkanoyl of 2 to 7 carbon atoms, alkenoyl of 3 to 7 carbon atoms, straight chain alkoxycarbonyl of 2 to 11 carbon atoms, branched chain alkoxycarbonyl of 4 to 11 carbon atoms, cycloalkoxycarbonyl of 4 to 11 carbon atoms, alkenoxycarbonyl of 2 to 11 carbon atoms, aralkoxycarbonyl of 6 to 12 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms; with the proviso that when $R_3$ is straight chain alkoxycarbonyl of 2 to 11 carbon atoms, branched chain alkoxycarbonyl of 4 to 11 carbon atoms, cycloalkoxycarbonyl of 4 to 11 carbon atoms, alkenoxycarbonyl of 2 to 11 carbon atoms or aralkoxycarbonyl of 6 to 12 carbon atoms,$R_2$ must be hydrogen;

A is a substituted phenyl group of the following formula:

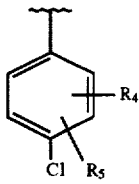

wherein:

$R_4$ and $R_5$ are, independently, cyano, nitro, amino, alkyl of 1 to 6 carbon atoms, perfluoroalkyl of 1 to 6 carbon atoms, fluoroalkyl of 1 to 6 carbon atoms, alkoxy of 1 to 6 carbon atoms, perfluoroalkoxy of 1 to 6 carbon atoms, fluoroalkoxy of 1 to 6 carbon atoms, alkylamino of 1 to 6 carbon atoms, dialkylamino of 2 to 12 carbon atoms, sulfamyl, alkylsulfonamido of 1 to 6 carbon atoms, arylsulfonamido of 6 to 12 carbon atoms, carbamoyl, alkylcarbamoyl of 2 to 7 carbon atoms, dialkylcarbamoyl of 4 to 14 carbon atoms, alkylcarboxamido containing 2 to 7 carbon atoms, arylcarboxamido containing 7 to 13 carbon atoms, alkylsulfonyl of 1 to 6 carbon atoms, perfluoroalkylsulfonyl of 1 to 6 carbon atoms, arylsulfonyl of 6 to 12 carbon atoms, chloro, bromo, fluoro, iodo, 1-imidazolyl, carboxyl or hydrogen, with the proviso that $R_4$ and $R_5$ cannot both be hydrogen;

or a pharmaceutically acceptable salt thereof.

2. A compound of claim 1 in which $R_1$ is straight chain alkyl of 1 to 10 carbon atoms, branched chain alkyl of 3 to 10 carbon atoms, fluoroalkyl of 1 to 10 carbon atoms or perfluoroalkyl of 1 to 10 carbon atoms;

$R_2$ and $R_3$ are, independently, hydrogen, alkanoyl of 2 to 7 carbon atoms, alkenoyl of 3 to 7 carbon atoms, aroyl of 7 to 12 carbon atoms, arylalkenoyl of 9 to 20 carbon atoms, straight chain alkoxycarbonyl of 2 to 7 carbon atoms, branched chain alkoxycarbonyl of 4 to 7 carbon atoms, alkenoxycarbonyl of 4 to 7 carbon atoms, or aralkoxycarbonyl of 6 to 12 carbon atoms; with the proviso that when $R_3$ is straight chain alkoxycarbonyl of 2 to 7 carbon atoms, branched chain alkoxycarbonyl of 4 to 7 carbon atoms, alkeiioxycarbonyl of 4 to 7 carbon atoms, or aralkoxycarbonyl of 6 to 12 carbon atoms, $R_2$ must be hydrogen;

A is a substituted phenyl group of the following formula:

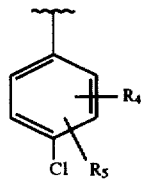

wherein:

$R_4$ and $R_5$ are, independently, cyano, alkyl of 1 to 6 carbon atoms, perfluoroalkyl of 1 to 6 carbon atoms, fluoroalkyl of 1 to 6 carbon atoms, alkoxy of 1 to 6 carbon atoms, perfluoroalkoxy of 1 to 6 carbon atoms, fluoroalkoxy of 1 to 6 carbon atoms, chloro, bromo, fluoro, iodo or hydrogen, with the proviso that $R_4$ and $R_5$ cannot both be hydrogen;

or a pharmaceutically acceptable salt thereof.

3. A compound of claim 1 in which $R_1$ is branched chain alkyl of 3 to 10 carbon atoms or fluoroalkyl of 1 to 10 carbon atoms;

$R_2$ and $R_3$ are, independently, hydrogen, alkanoyl of 2 to 7 carbon atoms, alkenoyl of 3 to 7 carbon atoms, straight chain alkoxycarbonyl of 3 or 5 carbon atoms, branched chain alkoxycarbonyl of 5 carbon atoms, alkenoxycarbonyl of 4 carbon atoms, or aralkoxycarbonyl of 8 carbon atoms; with the proviso that when $R_3$ is straight chain alkoxycarbonyl of 3 or 5 carbon atoms, branched chain alkoxycarbonyl of 5 carbon atoms, alkenoxycarbonyl of 4 carbon atoms, or aralkoxycarbonyl of 8 carbon atoms, $R_2$ must be hydrogen;

A is a substituted phenyl group of the following formula:

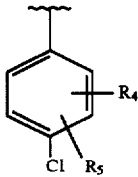

wherein:

$R_4$ and $R_5$ are, independently, cyano, methyl, ethyl, trifluoromethyl, fluoroalkyl of 1 to 2 carbon atoms, methoxy, ethoxy, trifluoromethoxy, fluoroalkoxy of 1 to 2 carbon atoms, chloro, bromo, fluoro or hydrogen, with the proviso that $R_4$ and $R_5$ cannot both be hydrogen;

or a pharmaceutically acceptable salt thereof.

4. The compound of claim 1 which is 3-(2,4-dichlorobenzylamino)-4-(1, 2,2-trimethylpropylamino)-cyclobut-3-ene-1,2-dione or a pharmaceutically acceptable salt thereof.

5. The compound of claim 1 which is 3-(2,4-dichloro-6-methyl-benzylamino)-4-(1,2,2-trimethyl-propylamino)-cyclobut-3-ene-1,2-dione or a pharmaceutically acceptable salt thereof.

6. The compound of claim 1 which is 3-(2,4-dichlorobenzylamino)-4-(1,1-dimethylpropylamino)-cyclobut-3-ene-1,2-dione or a pharmaceutically acceptable salt thereof.

7. The compound of claim 1 which is N-(2,4-dichlorobenzyl)-N-[2-(1,1-dimethyl-propylamino)-3,4-dioxo-cyclobut-1-enyl]-acetamide or a pharmaceutically acceptable salt thereof.

8. The compound of claim 1 which is N-(2,4-dichlorobenzyl)-N-[2-(1,1-dimethyl-propylamino)-3,4-dioxo-cyclobut-1-enyl]-butyramide or a pharmaceutically acceptable salt thereof.

9. The compound of claim 1 which is 3-(2,4-dichloro-6-methyl-benzylamino)-4-(1,1 -dimethyl-propylamino)-cyclobut-3-ene-1,2-dione or a pharmaceutically acceptable salt thereof.

10. The compound of claim 1 which is 3-(t-butylamino)-4-(2,4-dichlorobenzylamino)-cyclobut-3-ene-1,2-dione or a pharmaceutically acceptable salt thereof.

11. The compound of claim 1 which is 3-tert-butylamino-4-(2,4-dichloro-6-methyl-benzylamino)-cyclobut-3-ene-1, 2-dione or a pharmaceutically acceptable salt thereof.

12. The compound of claim 1 which is 3-(3,4-dichlorobenzylamino)-4-(1-ethyl-propylamino)-cyclobut-3-ene-1,2-dione or a pharmaceutically acceptable salt thereof.

13. The compound of claim 1 which is 3-(2,4-dichlorobenzylamino)-4-(1-ethyl-propylamino)-cyclobut-3-ene-1,2-dione or a pharmaceutically acceptable salt thereof.

14. The compound of claim 1 which is 3-(2,4-dichloro-6-methyl-benzylamino)-4-(2,2,3,3,3-pentafluoro-propylamnino)-cyclobut-3-ene-1,2-dione or a pharmaceutically acceptable salt thereof.

15. The compound of claim 1 which is N-(2,4-dichloro-6-methyl-benzyl)-N-[2-(1,1-dimethyl-propylamino)-3,4-dioxo-cyclobut-1-enyl]-butyramide or a pharmaceutically acceptable salt thereof.

16. The compound of claim 1 which is N-(2,4-dichloro-6-methyl-benzyl)-N-[2-(1,1-dimethyl-propylamino)-3,4-dioxo-cyclobut-1-enyl]-acetamide or a pharmaceutically acceptable salt thereof.

17. The compound of claim 1 which is N-(tert-butyl)-N-[2-(2,4-dichloro-6-methyl-benzylamino)-3,4-dioxo-cyclobut-1-enyl]-propionamide or a pharmaceutically acceptable salt thereof.

18. The compound of claim 1 which is 3-(2,4-dichloro-6-methyl-benzylamino)-4-(1,2-dimethyl-2-fluoro-propylamino)-cyclobut-3-ene-1,2-dione or a pharmaceutically acceptable salt thereof.

19. The compound of claim 1 which is 3-(2,4-dichlorobenzylarrdno)-4-(2-hydroxy-1,1-dimethylethylamino)-cyclobut-3-ene-1,2-dione or a pharmaceutically acceptable salt thereof.

20. The compound of claim 1 which is (R)-3-(2,4-dichlorobenzylarino)-4-(1,2,2-trimethylpropylamino)-cyclobut-3-ene-1,2-dione or a pharmaceutically acceptable salt thereof.

21. The compound of claim 1 which is 3-tert-butylamino-4-(3,4-dichlorobenzylamino)-cyclobut-3-ene-1,2-dione or a pharmaceutically acceptable salt thereof.

22. The compound of claim 1 which is 3-(3,4-dichlorobenzylamino)-4-(1,1-dimethylpropylamino)-cyclobut-3-ene-1,2-dione or a pharmaceutically acceptable salt thereof.

23. The compound of claim 1 which is (2,4-Dichloro-6-methyl-benzyl)-[2-(1,1-dimethyl-propylamino)-3,4-dioxo-cyclobut-1-enyl]-carbamic acid tert-butyl ester or a pharmaceutically acceptable salt thereof.

24. A pharmaceutical composition of matter comprising a compound of the formula:

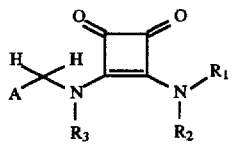

wherein:

$R_1$ is straight chain alkyl of 1 to 10 carbon atoms, branched chain alkyl of 3 to 10 carbon atoms, cycloalkyl of 3 to 10 carbon atoms, hydroxyalkyl of 2 to 10 carbon atoms, fluoroalkyl of 1 to 10 carbon atoms or polyfluoroalkyl of 1 to 10 carbon atoms;

$R_2$ and $R_3$ are, independently, hydrogen or an acyl stibstituent selected from the group consisting of formyl, alkanoyl of 2 to 7 carbon atoms, alkenoyl of 3 to 7 carbon atoms, straight chain alkoxycarbonyl of 2 to 11 carbon atoms, branched chain alkoxycarbonyl of 4 to 11 carbon atoms, cycloalkoxycarbonyl of 4 to 11 carbon atoms, alkenoxycarbonyl of 2 to 11 carbon atoms, aralkoxycarbonyl of 6 to 12 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms; with the proviso that when $R_3$ is straight chain alkoxycarbonyl of 2 to 11 carbon atoms, branched chain alkoxycarbonyl of 4 to 11 carbon atoms, cycloalkoxycarbonyl of 4 to 11 carbon atoms, alkenoxycarbonyl of 2 to 11 carbon atoms or aralkoxycarbonyl of 6 to 12 carbon atoms,$R_2$ must be hydrogen;

A is a substituted phenyl group of the following formula:

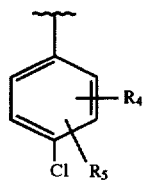

wherein:

$R_4$ and $R_5$ are, independently, cyano, nitro, amino, alkyl of 1 to 6 carbon atoms, perfluoroalkyl of 1 to 6 carbon atoms, fluoroalkyl of 1 to 6 carbon atoms, alkoxy of 1 to 6 carbon atoms, perfluoroalkoxy of 1 to 6 carbon atoms, fluoroalkoxy of 1 to 6 carbon atoms, alkylamino of 1 to 6 carbon atoms, dialkylamino of 2 to 12 carbon atoms, sulfamyl, alkylsulfonamido of 1 to 6 carbon atoms, arylsulfonamido of 6 to 12 carbon atoms, carbamoyl, alkylcarbamoyl of 2 to 7 carbon atoms, dialkylcarbamoyl of 4 to 14 carbon atoms, alkylcarboxamido containing 2 to 7 carbon atoms, arylcarboxamido containing 7 to 13 carbon atoms, alkylsulfonyl of 1 to 6 carbon atoms, perfluoroalkylsulfonyl of 1 to 6 carbon atoms, arylsulfonyl of 6 to 12 carbon atoms, chloro, bromo, fluoro, iodo, 1-imidazolyl, carboxyl or hydrogen, with the proviso that $R_4$ and $R_5$ cannot both be hydrogen;

or a pharmaceutically acceptable salt thereof and a pharmaceutically acceptable carrier therefor.

25. A method for reducing the adverse effects of smooth muscle contractions which comprises administering, orally or parenterally, to a patient in need thereof, a compound of the formula:

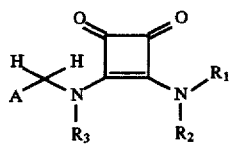

wherein:

$R_1$ is straight chain alkyl of 1 to 10 carbon atoms, branched chain alkyl of 3 to 10 carbon atoms, cycloalkyl of 3 to 10 carbon atoms, hydroxyalkyl of 2 to 10 carbon atoms, fluoroalkyl of 1 to 10 carbon atoms or polyfluoroalkyl of 1 to 10 carbon atoms;

$R_2$ and $R_3$ are, independently, hydrogen or an acyl substituent selected from the group consisting of formyl, alkanoyl of 2 to 7 carbon atoms, alkenoyl of 3 to 7 carbon atoms, straight chain alkoxycarbonyl of 2 to 11 carbon atoms, branched chain alkoxycarbonyl of 4 to 11 carbon atoms, cycloalkoxycarbonyl of 4 to 11 carbon atoms, alkenoxycarbonyl of 2 to 11 carbon atoms, aralkoxycarbonyl of 6 to 12 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms; with the proviso that when $R_3$ is straight chain alkoxycarbonyl of 2 to 11 carbon atoms, branched chain alkoxycarbonyl of 4 to 11 carbon atoms, cycloalkoxycarbonyl of 4 to 11 carbon atoms, alkenoxycarbonyl of 2 to 11 carbon atoms or aralkoxycarbonyl of 6 to 12 carbon atoms, $R_2$ must be hydrogen;

A is a substituted phenyl group of the following formula:

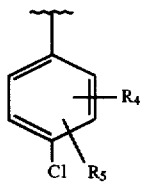

wherein:

$R_4$ and $R_5$ are, independently, cyano, nitro, amino, alkyl of 1 to 6 carbon atoms, perfluoroalkyl of 1 to 6 carbon atoms, fluoroalkyl of 1 to 6 carbon atoms, alkoxy of 1 to 6 carbon atoms, perfluoroalkoxy of 1 to 6 carbon atoms, fluoroalkoxy of 1 to 6 carbon atoms, alkylamino of 1 to 6 carbon atoms, dialkylamino of 2 to 12 carbon atoms, sulfamyl, alkylsulfonamido of 1 to 6 carbon atoms, arylsulfonamido of 6 to 12 carbon atoms, carbamoyl, alkylcarbamoyl of 2 to 7 carbon atoms, dialkylcarbamoyl of 4 to 14 carbon atoms, alkylcarboxamido containing 2 to 7 carbon atoms, arylcarboxamido containing 7 to 13 carbon atoms, alkylsulfonyl of 1 to 6 carbon atoms, perfluoroalkylsulfonyl of 1 to 6 carbon atoms, arylsulfonyl of 6 to 12 carbon atoms, chloro, bromo, fluoro, iodo, 1-imidazolyl, carboxyl or hydrogen, with the proviso that $R_4$ and $R_5$ cannot both be hydrogen;

or a pharmaceutically acceptable salt thereof.

26. The method of claim 25 in which the smooth muscle adversely contracting causes urinary incontinence.

27. The method of claim 25 in which the smooth muscle adversely contracting causes irritable bowel syndrome.

* * * * *

UNITED STATES PATENT AND TRADEMARK OFFICE
CERTIFICATE OF CORRECTION

PATENT NO. : 5,763,474
DATED : June 9, 1998
INVENTOR(S) : David R. Herbst et al.

Page 1 of 2

It is certified that error appears in the above-indentified patent and that said Letters Patent is hereby corrected as shown below:

| | |
|---|---|
| Col. 10 - line 40 | delete "3-pentaflouro-cyclobtut-3-ene –1,2-dione" insert "3-pentafluoro-cyclobut-3-ene-1,2-dione" |
| Col. 10 - line 42 | delete "4.2 mld., 28.4 mmol"; insert "4.2 mL., 28.4 mmol" |
| Col. 10 - line 42 | delete "pent afluoropropylaine"; insert "pentafluoropropylamine" |
| Col. 10 - line 43 | delete "28.4 snmol" ; insert "28.4 mmol" |
| Col. 10 - line 54 | delete "col pound"; insert "compound" |
| Col. 10 - line 64 | delete "-2propylamino)-" insert --[2-(1,1-dimethyl-propylamino)- --. |
| Col. 10 - line 64 | delete "3,4-dioxo-cyclobut-1-envl]"; insert "3,4-dioxo-cyclobut-1-enyl]" |
| Col. 10 - line 66 | delete "benzylamino -4i(1,1-" insert -- -benzyl-amino)-4-(1,1 --. |
| Col. 14 – line 50 | delete "trimethylpropylamino)-"; insert "trimethylpropylamino)-" |
| Col. 19 – line 52 | delete "alkeiioxycarbonyl"; insert "alkenoxycarbonyl" |
| Col. 21 – line 28 | delete "dichlorobenzylarrdno)"; insert "dichlorobenzylamino)" |

UNITED STATES PATENT AND TRADEMARK OFFICE
CERTIFICATE OF CORRECTION

PATENT NO. : 5,763,474
DATED : June 9, 1998
INVENTOR(S) : David R. Herbst et al.

It is certified that error appears in the above-indentified patent and that said Letters Patent is hereby corrected as shown below:

Col. 21 – line 32   delete "dichlorobenzylarino";   insert "dichlorobenzylamino"

Signed and Sealed this

Twenty-seventh Day of October, 1998

Attest:

BRUCE LEHMAN

*Attesting Officer*   *Commissioner of Patents and Trademarks*